United States Patent [19]
Lichkus et al.

[11] Patent Number: 5,989,621
[45] Date of Patent: Nov. 23, 1999

[54] DUAL CAPILLARY FIBER COATING PROCESS

[75] Inventors: Andrew Murray Lichkus, York, Pa.; Virginia Eleanor Schmidt, Danbury, Conn.

[73] Assignee: Sherwood Services AG, Schwertstrasse 9, Switzerland

[21] Appl. No.: 09/027,656

[22] Filed: Feb. 23, 1998

Related U.S. Application Data

[60] Provisional application No. 60/041,197, Mar. 25, 1997.

[51] Int. Cl.[6] ............................. B05D 3/00; A61L 17/00
[52] U.S. Cl. .................. 427/2.31; 427/384; 427/363; 427/434.2; 606/228
[58] Field of Search ................. 427/2.31, 2.29, 427/384, 385.5, 363, 430.1, 434.2; 606/228

[56] References Cited

U.S. PATENT DOCUMENTS

| | | | |
|---|---|---|---|
| 3,867,190 | 2/1975 | Schmitt et al. | 427/2.31 |
| 4,185,637 | 1/1980 | Mattei | 427/2.31 |
| 4,711,241 | 12/1987 | Lehmann | 427/2.31 |
| 5,104,398 | 4/1992 | Planck et al. | 427/2.31 |
| 5,123,912 | 6/1992 | Kaplan et al. | 427/2.31 |
| 5,352,515 | 10/1994 | Jarrett et al. | 428/357 |
| 5,447,966 | 9/1995 | Hermes et al. | 424/430 |
| 5,643,628 | 7/1997 | Sondregger | 427/2.31 |

*Primary Examiner*—Shrive Beck
*Assistant Examiner*—Bret Chen

[57] ABSTRACT

A method for coating surgical fibers and surgical braids employing dual capillaries (10) in series. After the fiber (50) or braid is initially coated with a t-guide capillary (16), the fiber (50) or braid is dried using forced air within an enclosure (66) and then coated a second time by the second capillary (14), a v-guide capillary (52).

16 Claims, 6 Drawing Sheets

DUAL CAPILLARY FIBER COATING PROCESS

CROSS-REFERENCE TO RELATED APPLICATIONS

This Patent Application claims the benefit of U.S. Provisional Application No. 60/041,197 filed Mar. 25, 1997, the contents of which are incorporated herein by reference in its entirety.

BACKGROUND OF THE INVENTION

1. Field of the Invention

This invention relates to coating surgical fibers or surgical braids and, more particularly, to using dual capillaries to coat surgical fibers or braids to achieve unexpected results as evidenced by unexpectedly favorable reductions in the value of the coefficient of friction.

2. Related Art

A suture is used to sew tissue together, often during surgery. Often, the suture is comprised of a filament and a coating around the filament. The filament may be a monofilament-type or a braid-type.

The coating around a filament is critical to the performance of the suture. Specifically, an evenly coated fiber insures predictable and repeatable performance of the suture in surgery. As a length of suture is pulled through tissue, a certain amount of tissue drag is experienced. Excessive tissue drag can cause trauma to the tissue, and is therefore undesirable. The coefficient of friction of a suture is directly proportional to tissue drag and is an indicator of an evenly coated fiber. An evenly coated fiber has a lower coefficient of friction; an unevenly coated fiber has a higher coefficient of friction.

To determine generally whether a particular suture has a predictable even coating, the coefficient of friction is tested for a large number of suture samples. As shown in FIG. 1, test results indicating the coefficient of friction for multiple sample of sutures are illustrated. The reference suture in FIG. 1 is a coated suture currently available to the public. The non-coated fiber in FIG. 1 is a polybutester filament. The coated fiber referred to in FIG. 1 refers to a coated suture also available to the public. FIG. 1 illustrates that coated fibers such as the reference suture and the coated fiber generally provide improved performance, as well as predictable and repeatable performance as reflected in the coefficient of friction values, over non-coated filament. Accordingly, coated surgical sutures are often preferred over non-coated surgical sutures.

FIG. 2 illustrates coefficient of friction values for non-coated surgical filaments of size 7-0 and coated surgical fiber of size 7-0. As is evident from FIG. 2, the mean and the median coefficient of friction of the coated fiber is significantly lower than the mean and median coefficient of friction of the non-coated surgical fiber. However, it is also evident that the coated surgical fiber shows a large variation in the coefficient of friction among the samples tested. Variation in the coefficient in friction among various samples, especially a large variation, is an indication that the coating is applied unevenly and/or sections of surgical suture are not being coated. For example, the data points for coated surgical fibers within the coefficient of friction range of 7.5 to 8.2 indicate or strongly suggest that there has been some failure to uniformly coat the surgical fiber.

The coated surgical fibers (or surgical sutures) referred to in FIGS. 1 and 2 were coated using a single capillary process. In particular, a capillary tube is provided with a source of polymer coating material generally in the form of a polymer-in-solvent solution. A non-coated filament is then drawn across the capillary tube. As the filament is drawn across the capillary tube, a polymer-in-solvent solution is deposited on the surgical suture. When the solvent evaporates, only the polymer is left coating the filament.

Should an air bubble enter the capillary tube, a volume of polymer-in solvent solution would be displaced. Accordingly, as the fiber is drawn across the tube, the air bubble in the tube would be drawn towards the fiber until ultimately, the filament would come into contact with the air bubble and a portion of the filament in contact with the air bubble would remain uncoated for the length of time it takes or the air bubble to pass. Other potential sources of uneven coating include when the volume of polymer-in-solvent solution from the capillary tube is deposited unevenly on the filament.

Accordingly, there is a need in the art to provide a process for coating a filament which will produce a coated surgical suture which insures predictable and repeatable performance by being coated evenly.

There is a further need in the art to provide a process for coating a filament for a surgical suture which has a coated coefficient of friction which is consistently lower than that currently taught in the art.

SUMMARY OF THE INVENTION

It is in the view of the above problems that the present invention was developed. The invention is a method and apparatus for applying a coating to a filament to make a surgical suture. The term "filament" includes a monofilament-type and a braid-type filament. The apparatus and method employs two capillary devices in series. In the preferred embodiment, the first capillary device pre-wets a filament with a polymer-in-solvent solution at a solvent concentration which is approximately one-half of the concentration of that used in a conventional single capillary process. After pre-wetting in the first capillary device, the filament is exposed to a positive air flow from a forced air source and dries. Immediately, the filament enters a second capillary device which applies a polymer-in-solvent solution at a concentration of approximately one half that used in a single capillary process. This method and apparatus for coating a filament yields unexpected results in the form of unexpectedly favorable reductions in the values of the coefficient of friction, as well as a significantly reduced range in the values of the coefficient of friction as tested over hundreds of surgical suture samples.

The method and apparatus of the present invention may be applied to any filament, including a monofilament or a braid, to make a surgical suture.

Further features and advantages of the present invention, as well as the structure and operation of various embodiments of the present invention, are described below in detail with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings.

DETAILED DESCRIPTION OF THE PREFERRED EMBODIMENTS

Figure 1:
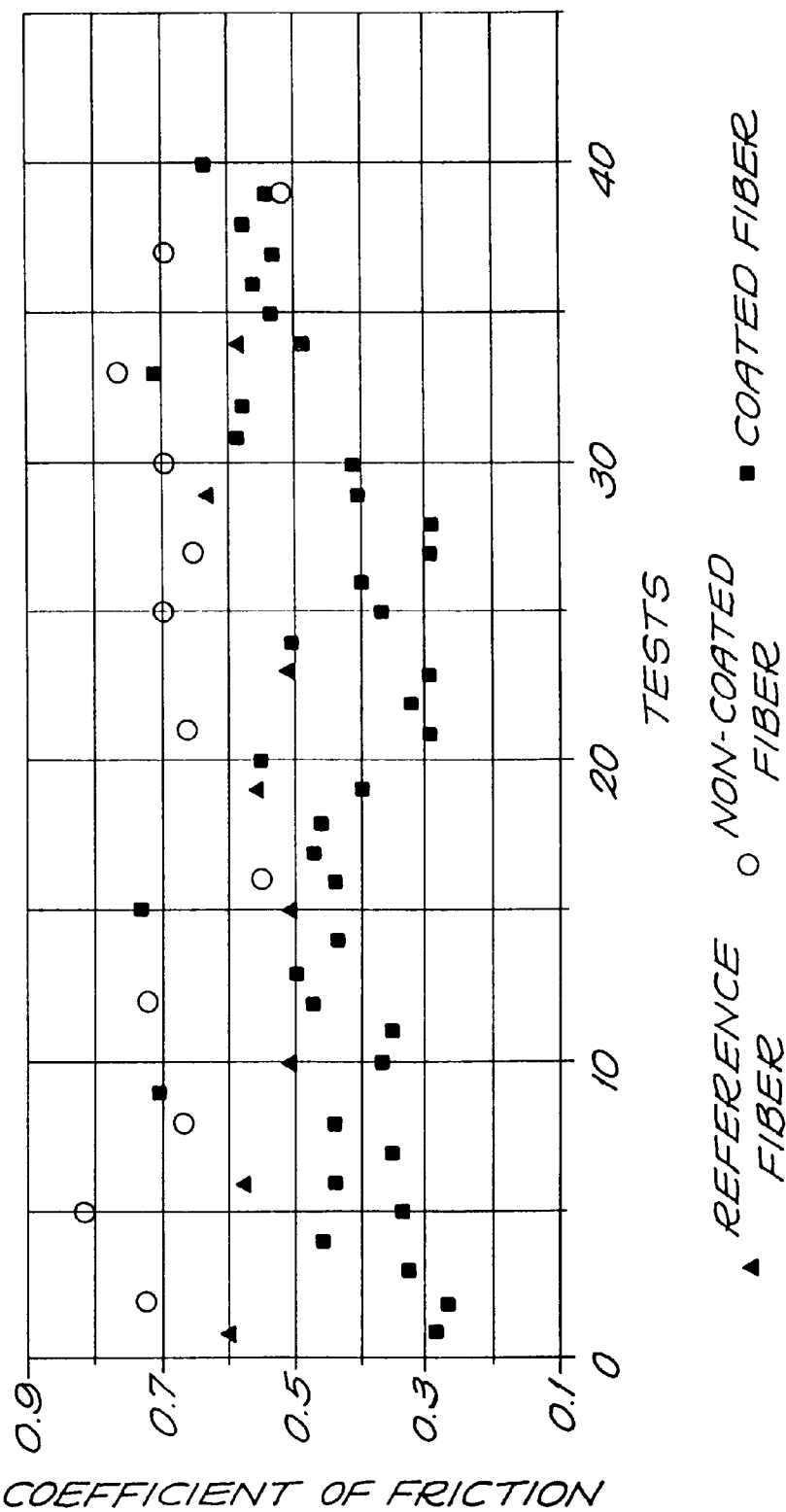
FIG. 1 illustrates a graph of test points showing the coefficient of friction for polybutester fibers, both non-coated and coated using a single capillary process.
Figure 2:
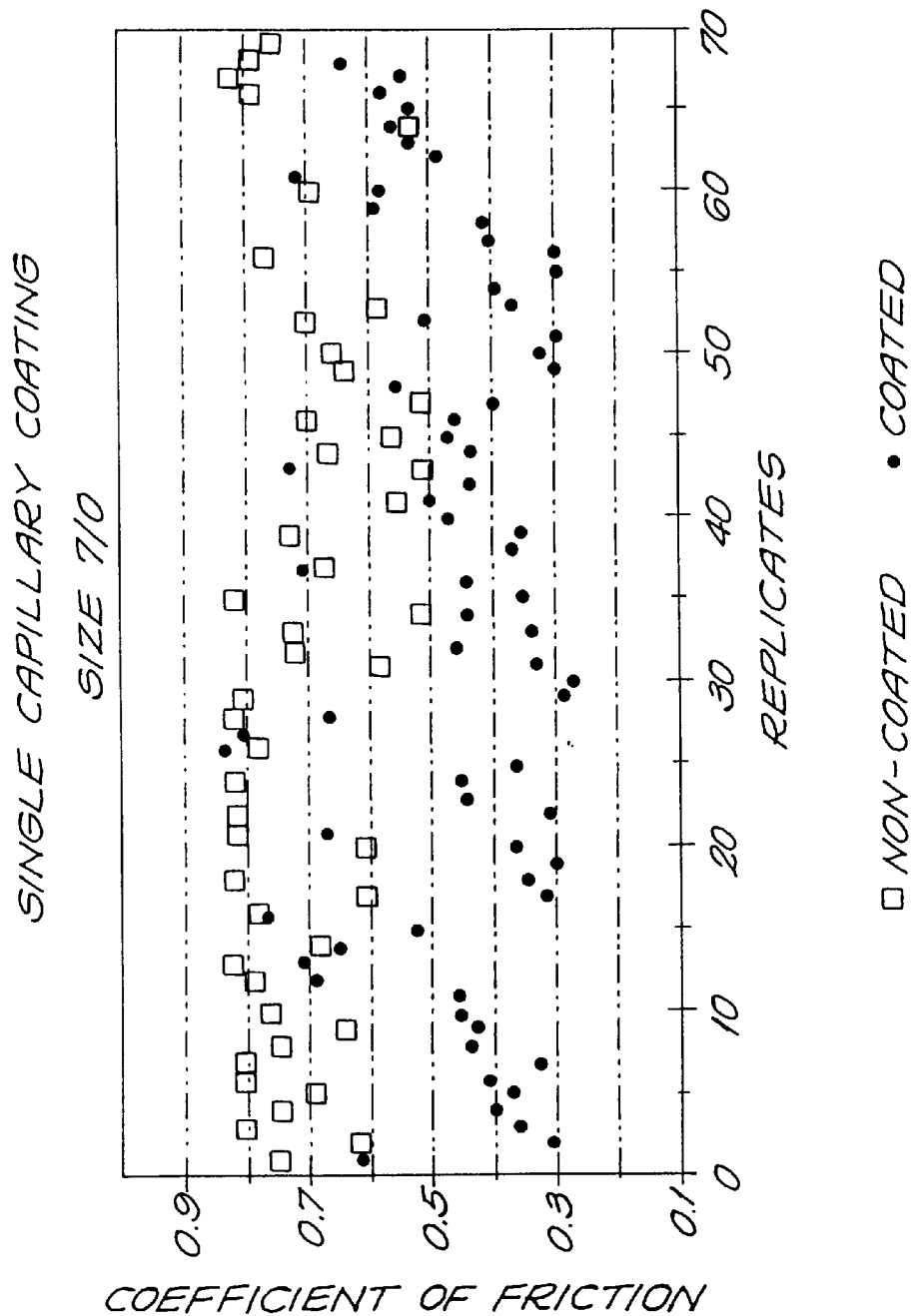
FIG. 2 illustrates a graph of test points showing the coefficient of friction for a size 7-0 filament, both non-coated and coated using a single capillary process.
Figure 3:
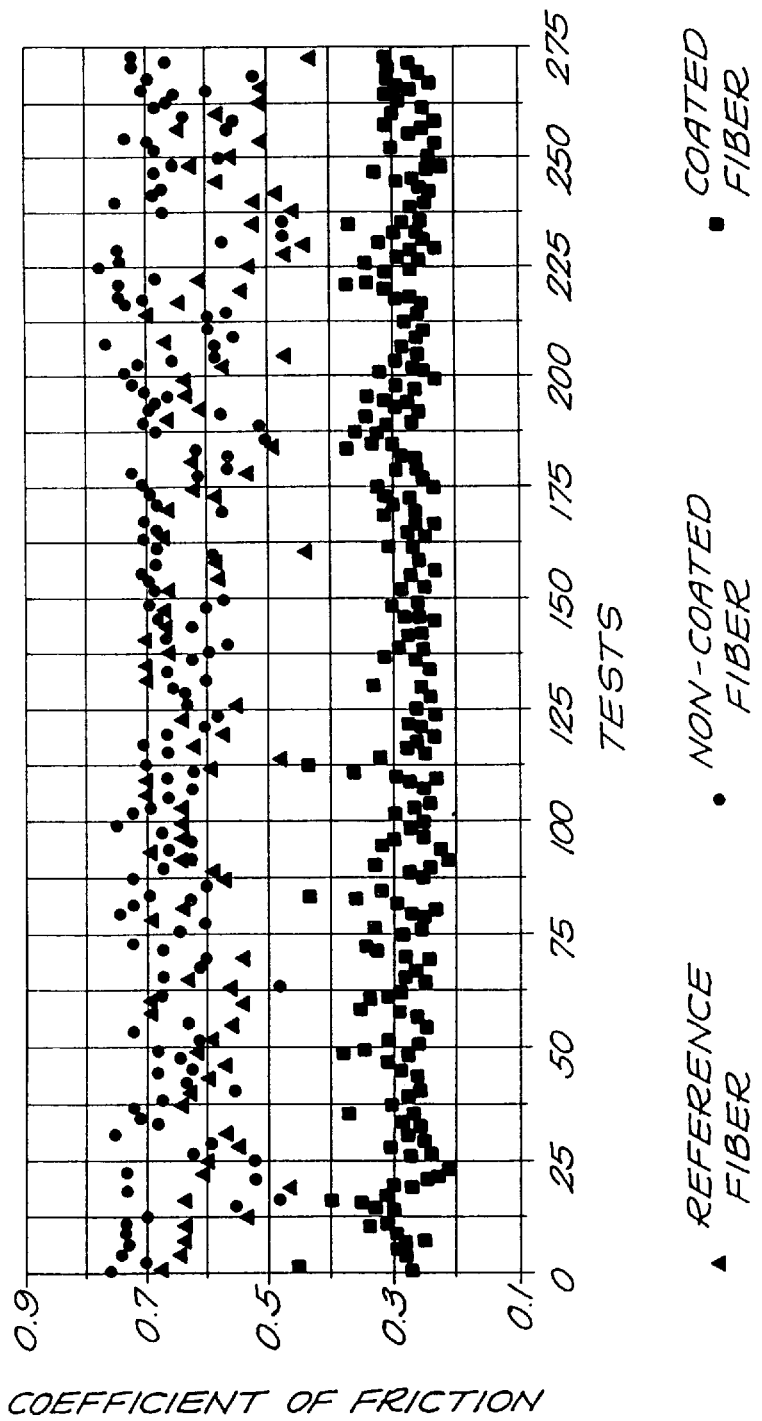
FIG. 3 illustrates a graph of test points showing the coefficient of friction for polybutester fibers, including the product sold under the trade name PROLENE, non-coated fibers, and coated fibers using a dual capillary process of the present invention.
Figure 4:
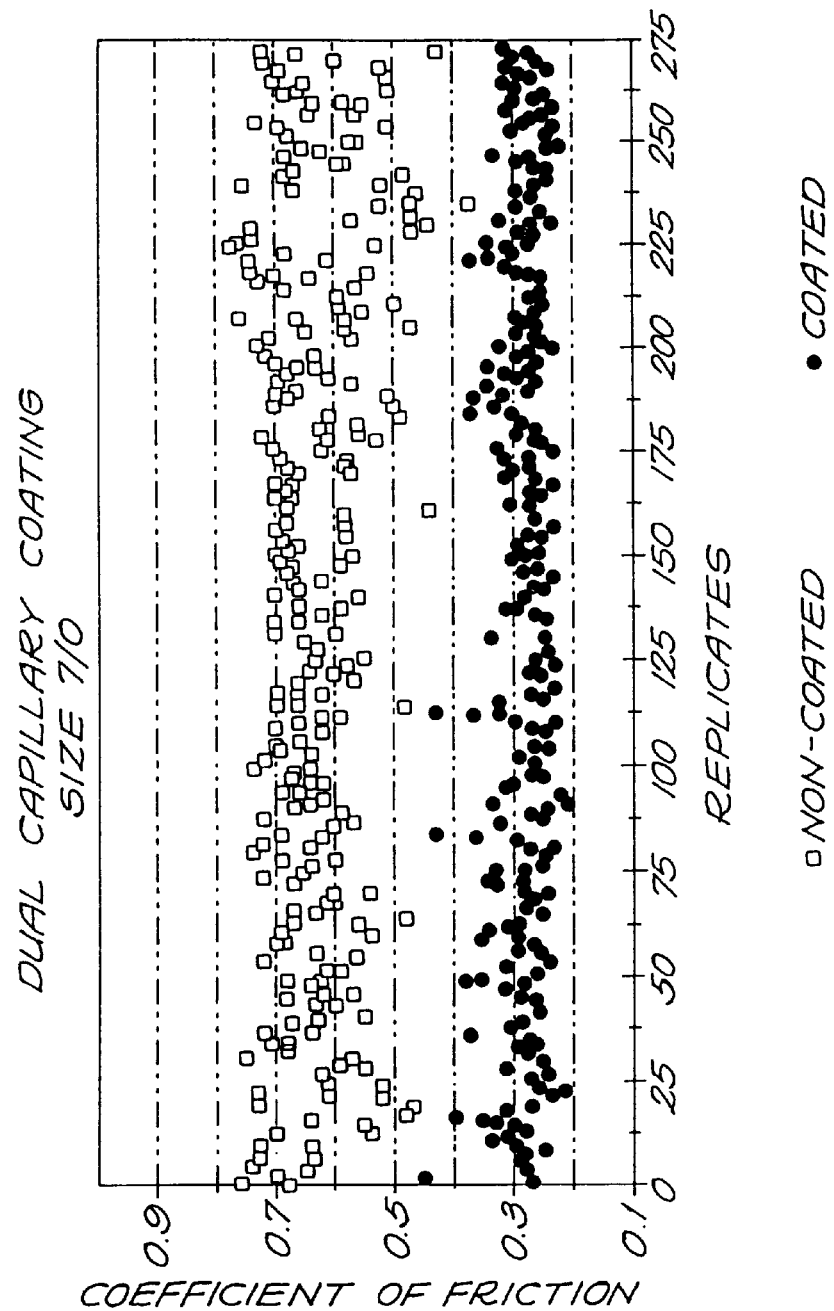
FIG. 4 illustrates a graph of test points showing the coefficient of friction for a size 7-0 filament, both non-coated and coated using a dual capillary process of the present invention.

Referring to the accompanying drawings in which like reference numbers indicate like elements, FIGS. 3 and 4 show the coefficient of friction results achieved using the dual capillary of the present invention. As shown in FIG. 3, the PROLENE suture and the non-coated fiber information as well as the non-coated fiber information in FIG. 4 are identical to those shown in FIGS. 1 and 2. The coated fiber referred to in FIGS. 3 and 4 are coated using the dual capillary process of the present invention. As is easily seen with coated fibers generally in FIG. 3, and with the coated fibers sized 7-0 specifically, an unexpected improvement in the coefficient of friction and an unexpected reduction in the variable range of the coefficient of friction is achieved using the dual capillary process of the present invention. Based on these test results, it is clear that the dual capillary process of the present invention attains the advantage of insuring predictable and repeatable performance derived from uniformity and quality of product.

The test values of the coefficient of friction were obtained by carefully following the methods disclosed in Examples 5 and 6 of U.S. Pat. No. 5,442,016, which is hereby incorporated by reference in its entirety. Specifically, the coefficient of friction ($\mu$) was calculated using the following formula:

$$\mu = F/N$$

where

F=ascending force—descending force

N=ascending force+descending force

As stated above, test data was obtained by carefully following the methods described in Examples 5 and 6 of U.S. Pat. No. 5,442,016. The value for $\mu$ was determined for each cycle of the test (a cycle is defined as one ascending pass and one descending pass) and a total of three cycles was run for each sample. From these values, the chart in FIG. 4 was obtained.

Figure 5:
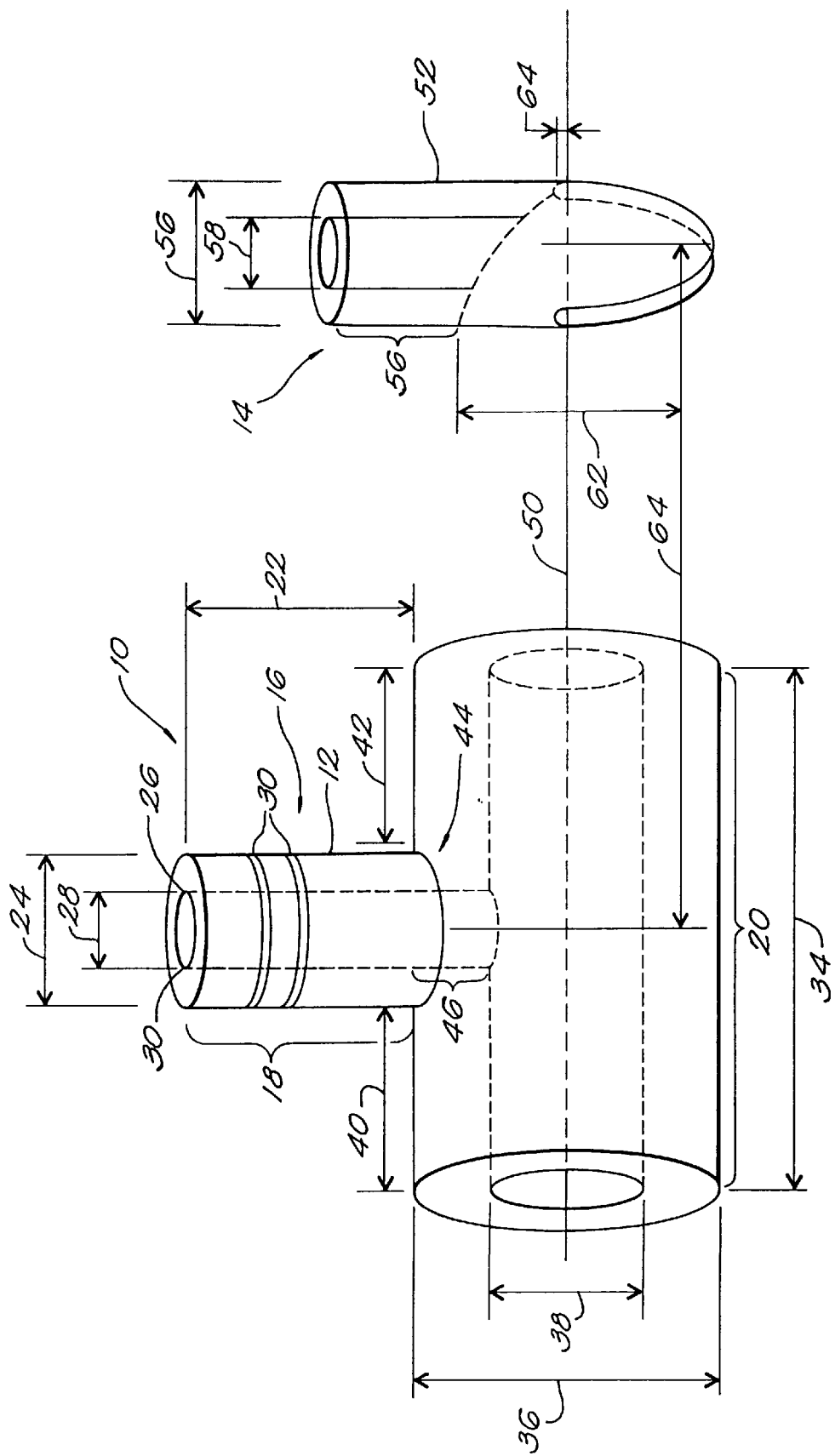
FIG. 5 illustrates a configuration of guides in a dual capillary arrangement for coating fibers and braids in accordance with a preferred embodiment of the present invention.

In FIG. 5, a method and apparatus for using a dual capillary process is illustrated that achieves the results shown in FIGS. 3 and 4.

The dual capillary apparatus is shown generally at 10. Dual capillary apparatus comprises first capillary device 12 and second capillary device 14. First capillary device 12 is t-shaped and, because there is no prior art analog to this device 12 in the surgical suture coatings art, is termed a "t-guide" shown generally at 16. T-guide 16 has a vertical cylindrical portion 18 and a horizontal cylindrical portion 20 in a preferred embodiment. Vertical cylindrical portion 18 has a length 22 of 18 mm and an outside diameter 24 of 3 mm. Extending through the center of vertical cylindrical portion 18 is a centered vertical circular bore 26 having a diameter 28 of 3 mm extending therethrough. Threads 30 are provided on the upper portion of vertical cylindrical portion 18. Threads 30 are adapted to engage the enclosure shown in FIG. 6. In FIG. 5, horizontal cylindrical portion 20 of t-guide 16 has a length 34 in the preferred embodiment of 16 mm, an outer diameter 36 of 5 mm, and a horizontal circular bore 38 of 3 mm diameter in the center extending therethrough. Horizontal cylindrical portion 20 has a forward portion 40 of length 5 mm and a rearward portion 42 also of 5 mm. Middle portion 44 of horizontal cylindrical portion 20 is adapted to receive one end of vertical cylindrical portion 18. Middle portion 44 is further adapted to continue centered vertical circular bore 26 of vertical cylindrical portion 18 through horizontal cylindrical portion 20 via bore portion 46 which extends from one end of vertical cylindrical portion 18 to horizontal cylindrical bore 38. A filament 50 which may be monofilament-type or braid-type is shown extending through horizontal circular bore 38 of horizontal cylindrical portion 20.

Second capillary device show generally at 14 is specifically known in the art as a v-guide 52. V-guide 52 has an overall length in the preferred embodiment of 28 mm. V-guide 52 has a first cylindrical portion 56 having an outer diameter 58 of approximately 6.2 mm and a centered vertical circular bore 58 extending there through of approximately 0.6 mm.

Second portion 60 of v-guide 52 has staggered v-fins extending downwardly. Specifically, the v-fins on one side extend downwardly at 62 for 8 mm and extend downwardly at the other side at 64 for 3 mm. The distance between the center of centered vertical bore 26 of vertical cylindrical portion 18 and the center of centered vertical circular bore 58 of v-guide 52 is shown at 64 and in the preferred embodiment is 15 inches.

Preferably, t-guide 16 is made from clear polypropylene or any other material which will not react with a solvent used to dissolve the polymer-in-solvent solution applied to filament 50. Again, it should be made clear that filament 50 generically refers to a monofilament or a braid filament. After coating, filament 50 may be generically referred to as a surgical suture.

Figure 6:
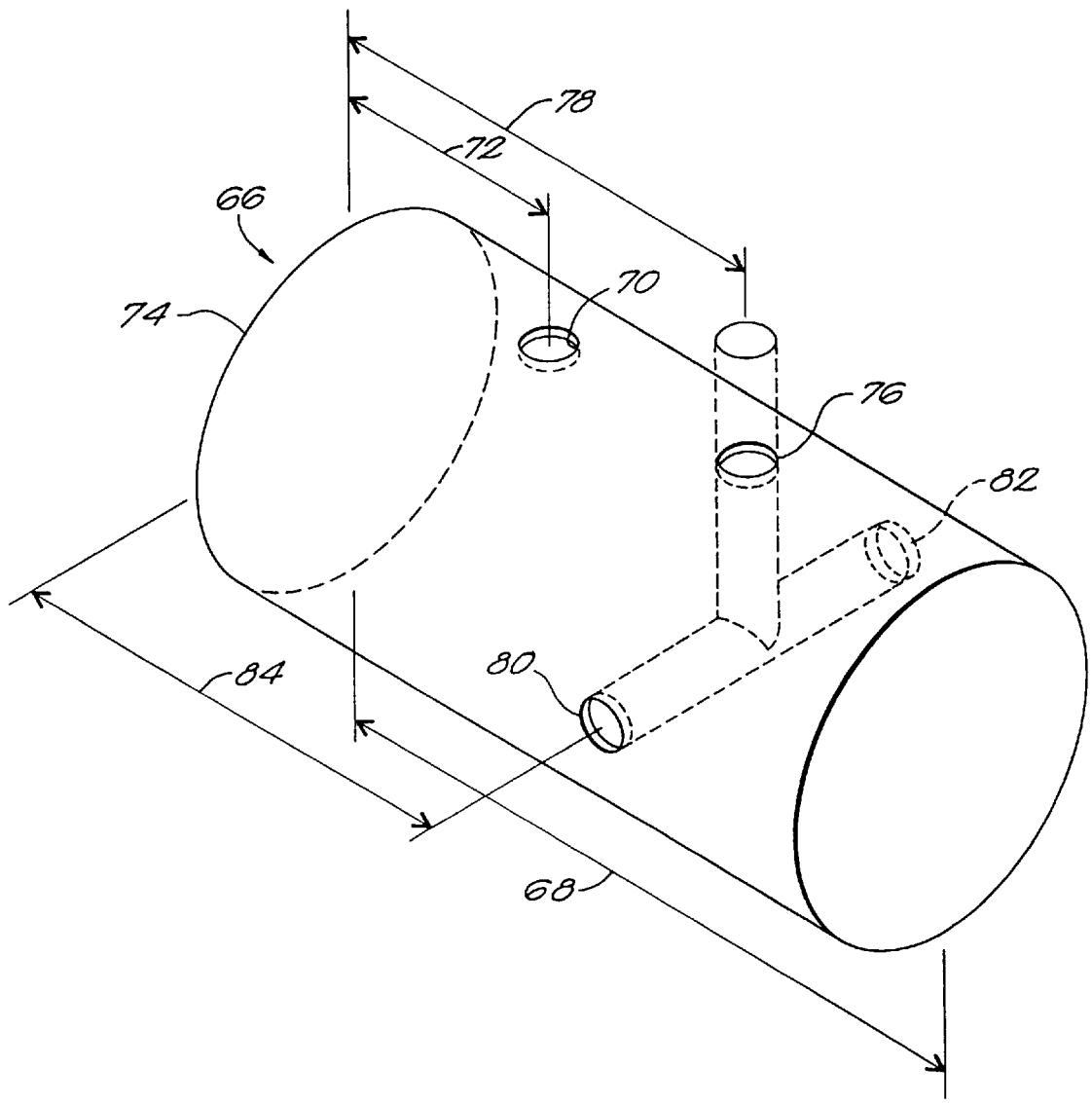
FIG. 6 illustrates placement of one guide within an enclosure to provide for forced air drying in accordance a preferred embodiment of the present invention.

FIG. 6 shows a preferred embodiment in which t-guide 16 is shown in phantom disposed within an enclosure shown generally at 66. The function of enclosure 66 is to provide a means for permitting a forced air source to direct a positive air flow over filament 50 after it exits from rearward portion 42 of horizontal cylindrical portion 20. As illustrated in FIG. 6, enclosure 66 is cylindrical and has an overall length 68 of 7 inches. Enclosure 66 defines a first hole 70 for receiving an air line (not shown). The center of first hole 70 is disposed at a distance 72 of approximately 3 inches from first end 74. Second hole 76 is adapted to receive t-guide 16, and more specifically, threads 30 of t-guide 16. The center of second hole 76 is disposed at second distance 78 of approximately 5½ inches from first end 74 in the preferred embodiment. At 90 degrees from second hole 76, enclosure 66 defines 3rd and 4th holes, (shown in phantom) 80 and 82 respectively. The purpose of 3rd and 4th holes 80 and 82 are to permit filament 50 to extend through enclosure 66 and also through horizontal cylindrical portion 20 of t-guide 16. Preferably, 3rd and 4th holes 80 and 82 respectively are disposed a distance 84 of 5½ inches from first end 74.

When an air source (not shown) is introduced at first hole 70, a positive air flow is experienced between the end of rearward portion 42 of horizontal cylindrical portion 20 of t-guide 16 and 4th hole 82 of enclosure 66. This positive air flow serves to assist in drying filament 50 after polymer-in-solvent solution is applied to it from t-guide 16.

In operation, t-guide 16 is provided with polymer-in-solvent solution at a rate of 1 ml per minute. The polymer-in-solvent solution is a polytribolate copolymer at a solvent concentration of 3–5% by weight in acetone. The polytribolate copolymer is formed from 3 repeat units: 9% glycolate, 51% $\epsilon$-caprolactone, and 40% poloxamer 188. Similarly, v-guide 52 is also provided with the same polymer-in-solvent solution at the same rate. T-guide 16 is disposed in enclosure 66. Filament 50 is drawn through enclosure 66, t-guide 16, and v-guide 52 at a preferable rate of 50 feet per minute.

As filament 50 is drawn through horizontal cylindrical portion 20 of t-guide 16, the polymer-in-solvent solution is provided to vertical cylindrical portion 18 of t-guide 16 and the polymer-in-solvent solution travels downwardly through vertical bore 26 until it reaches horizontal circular bore 38. When the polymer-in-solvent solution reaches horizontal circular bore 38, it comes into contact with filament 50 and thereafter, coats filament 50. The fact that the polymer-in-solvent solution goes into horizontal cylindrical portion 20 is important because any air bubbles (not shown) which may have traveled through vertical cylindrical portion 18 are mitigated within horizontal circular bore 38. Specifically, the air bubble can split in half with one half moving to the forward portion 40 and the other half moving to the rearward portion 42. Splitting the air bubble minimizes the gap in polymer-in-solvent solution, alternatively, because any air bubble would be unlikely to occupy the entire volume of horizontal circular bore 38, some polymer-in-solvent solution will be applied to filament 50. Upon exiting rearward portion 42 of horizontal cylindrical portion 20 of t-guide 16, filament 50 is exposed to a positive air flow from a forced air source which assists in drying the polymer-in-solvent coating applied by t-guide 16. Next, within approximately 13 inches from exiting t-guide 16, filament 50 enters v-guide 52 where upon the same polymer-in-solvent solution is applied to filament 50. Upon exiting v-guide 52, filament 50 is dried as is well known in the art.

By coating filaments in the manner shown and described above, unexpected and superior results are obtained as evidenced by the significant decrease in the test data values of the coefficient of friction.

In view of the foregoing, it will be seen that the several objects of the invention are achieved and other advantages are attained. The embodiments were chosen and described in order to best explain the principles of the invention and its practical application to thereby enable others skilled in the art to best utilize the invention in various embodiments and with various modifications as are suited to the particular use contemplated. As various modifications could be made in the constructions and methods herein described and illustrated without departing from the scope of the invention, it is intended that all matter contained in the foregoing description or shown in the accompanying drawings shall be interpreted as illustrative rather than limiting. For example, first capillary device 12 and second capillary device 14 could comprise dual t-guide capillaries similar to that referred to by reference numeral 16. Another modification falling within the scope of the present invention involves lengthening the dimensions of horizontal cylindrical portion 20 of t-guide 16, or any other dimensions of the guides. Thus, the breadth and scope of the present invention should not be limited by any of the above-described exemplary embodiments, but should be defined only in accordance with the following claims appended hereto and their equivalents.

What is claimed is:

1. A method of coating a surgical filament or braid comprising:

(A) disposing a t-guide, having vertical and horizontal cylindrical portions, a fixed distance from a second guide;

(B) providing said t-guide with a first polymer-in-solvent solution;

(C) providing said second guide with a second polymer-in-solvent solution;

(D) drawing said filament or braid through said t-guide while simultaneously applying said first polymer-in-solvent solution to said surgical filament or braid;

(E) drying said filament or braid; and (F) drawing said filament or braid through said second guide while simultaneously applying said second polymer-in-solvent solution to said filament or braid.

2. The method of claim 1, wherein said filament is size 7-0.

3. The method of claim 1, wherein said filament is size 8-0.

4. The method of claim 1, wherein said filament is a polybutester fiber.

5. The method of claim 1, wherein said fixed distance is 15 inches.

6. The method of claim 1, wherein said first polymer-in-solvent solution is a polytribolate copolymer at a concentration of 3–5% by weight in acetone, and said polytribolate copolymer is formed from three repeat units: 9% glycolate, 51% $\epsilon$-caprolactone, and 40% poloxamer 188.

7. The method of claim 1, wherein said first and second polymer-in-solvent solutions are the same.

8. The method of claim 1, wherein said second guide is a v-guide.

9. The method of claim 1, further comprising the steps of:

providing said t-guide with a vertical cylinder 18 mm long having an outer diameter of 6 mm and a vertical circular bore of 3 mm diameter in the center extending therethrough;

providing said t-guide with a horizontal cylinder 16 mm long having an outer diameter of 5 mm and a horizontal circular bore of 3 mm diameter in the center extending therethrough; and adapting said horizontal cylinder of said t-guide to receive one end of said vertical cylinder and to continue said vertical circular bore of said vertical cylinder through said horizontal cylinder to meet said horizontal circular bore of said horizontal cylinder.

10. The method of claim 1, further comprising:

providing said t-guide with polymer-in-solvent solution at a rate of 1 ml per minute.

11. The method of claim 1, further comprising:

providing said second guide with polymer-in-solvent solution at a rate of 1 ml per minute.

12. The method of claim 1, further comprising:
drawing said surgical filament or braid at a rate of 50 feet per minute.

13. The method of claim 1, further comprising:
providing an enclosure with a forced air source;
disposing said t-guide in said enclosure such that said filament exiting said t-guide is exposed to a positive air flow from said forced air source.

14. The method of claim 13, further comprising:
providing said enclosure with cylindrical outer dimensions of 7 inches in length;
defining a first hole by said enclosure adapted to receive an air source 3 inches from a first end of said enclosure;
defining a second hole by said enclosure adapted to receive a source of polymer-in-solvent solution 5½ inches from said first end of said enclosure;
defining third and fourth holes by said enclosure adapted to permit linear passage of said filament 5½ inches from said first end of said enclosure.

15. A method of coating a filament comprising:
drawing said filament through a t-guide;
applying a first coating to said filament;
drying said first coating;
applying a second coating to said filament such that said filament is substantially uniformly coated having a coefficient of friction less than 0.26 over substantially an entire length of said filament.

16. A method according to claim 15, wherein said filament is size 7-0 and said coefficient of friction is always less than 0.5.

* * * * *